(12) United States Patent
Yoshimura et al.

(10) Patent No.: US 12,023,204 B2
(45) Date of Patent: Jul. 2, 2024

(54) DISTANCE-MEASURING METHOD AND ENDOSCOPIC SYSTEM

(71) Applicant: OLYMPUS CORPORATION, Tokyo (JP)

(72) Inventors: Katsuhiko Yoshimura, Koganei (JP); Kazunori Tokiwa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 588 days.

(21) Appl. No.: 17/216,182

(22) Filed: Mar. 29, 2021

(65) Prior Publication Data

US 2021/0212790 A1   Jul. 15, 2021

Related U.S. Application Data

(63) Continuation of application No. PCT/JP2018/037402, filed on Oct. 5, 2018.

(51) Int. Cl.
*A61B 90/00*   (2016.01)
*A61B 1/00*   (2006.01)
(Continued)

(52) U.S. Cl.
CPC .......... *A61B 90/06* (2016.02); *A61B 1/00006* (2013.01); *A61B 5/065* (2013.01);
(Continued)

(58) Field of Classification Search
CPC ..... A61B 90/06; A61B 1/00006; A61B 5/065; A61B 2090/061; A61B 2090/067;
(Continued)

(56) References Cited

U.S. PATENT DOCUMENTS

2007/0265502 A1* 11/2007 Minosawa ......... A61B 1/00177
600/173
2010/0094312 A1* 4/2010 Ruiz Morales ........ A61B 34/70
73/504.03
(Continued)

FOREIGN PATENT DOCUMENTS

JP           4382894 B2    12/2009
JP       2013-509902 A     3/2013
(Continued)

OTHER PUBLICATIONS

International Search Report dated Dec. 11, 2018 received in PCT/JP2018/037402.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

A distance-measuring method includes acquiring a first curvature angle of a curved portion in a first state in which an endoscope is inserted into a body cavity and captures an observation target, a second curvature angle of the curved portion in a second state in which an insertion direction of the endoscope is changed with a position of a trocar as a pivot point while capturing the same observation target as in the first state, a change amount in an insertion angle due to a change in the insertion direction, and an insertion amount of the endoscope from the pivot point of the trocar to the curved portion, so as to calculate a distance from a distal end portion of the endoscope to the observation target in a state in which the endoscope is inserted into the body cavity via the trocar.

16 Claims, 18 Drawing Sheets

(51) Int. Cl.
    *A61B 1/313*     (2006.01)
    *A61B 5/06*     (2006.01)

(52) U.S. Cl.
    CPC ....... *A61B 1/3132* (2013.01); *A61B 2090/061* (2016.02); *A61B 2090/067* (2016.02)

(58) Field of Classification Search
    CPC .............. A61B 1/3132; A61B 1/00149; A61B 1/00183; A61B 190/361; A61B 2090/062
    USPC .................................. 600/117, 424; 606/130
    See application file for complete search history.

(56) References Cited

U.S. PATENT DOCUMENTS

| | | | |
|---|---|---|---|
| 2012/0209069 A1 | 8/2012 | Popovic et al. | |
| 2014/0303437 A1* | 10/2014 | Kikuchi | A61B 1/00193 600/106 |
| 2015/0327940 A1* | 11/2015 | Inoue | A61B 34/30 606/130 |
| 2016/0213364 A1* | 7/2016 | Inoue | A61B 1/008 |
| 2019/0167079 A1* | 6/2019 | Inoue | A61B 34/30 |
| 2019/0274524 A1* | 9/2019 | Nagao | A61B 1/00149 |
| 2019/0328469 A1* | 10/2019 | Ando | A61B 34/30 |

FOREIGN PATENT DOCUMENTS

| | | |
|---|---|---|
| JP | 2015-123201 A | 7/2015 |
| JP | 6091410 B2 | 3/2017 |
| JP | 2018-007840 A | 1/2018 |
| WO | 2013/108776 A1 | 7/2013 |

\* cited by examiner

DISTANCE-MEASURING METHOD AND ENDOSCOPIC SYSTEM

CROSS REFERENCE TO RELATED APPLICATIONS

This application is a continuation application based on a PCT Patent Application No. PCT/JP2018/037402, filed on Oct. 5, 2018, the entire content of which is hereby incorporated by reference.

BACKGROUND

Technical Field

The present invention relates to a distance-measuring method and an endoscopic system that is inserted into a patient's body to observe inside the patient's body in a surgical operation.

Background Art

Currently, laparoscopic surgery is performed in which a trocar is inserted into the patient's body, various medical devices are inserted from the trocar, and various treatments and examinations are performed inside the patient's body. This laparoscopic surgery requires a small incision on the patient's body surface, which reduces the burden on the patient. On the other hand, it is necessary to perform the operation while observing the patient's body with an endoscope. Therefore, it is necessary to improve the visibility and operability of medical instruments.

As a method of providing the desired field of view by the operator, there is a way to control the endoscope in which the position specified by the operator on the screen or the position required by the operator is estimated from the image information, and the position is set to a predetermined area on the screen, for example, the center of the screen. For example, Japanese Patent (Granted) Publication No. 4382894 (hereinafter referred to as Patent Document 1) discloses an endoscope system that reads the position of a marker attached to a treatment tool by image processing and changes the field of view of the endoscope by following the movement of the treatment tool based on the position information. In this endoscope system, the arm holding the endoscope is controlled.

As described above, the control method for setting the operation parameters of the controllable operation target such as the arm by using the visual input (image input) is called "visual servo" or "visual feedback control". In a visual servo as in Patent Document 1, a simple visual field operation such as bringing a designated target on the screen to a predetermined position such as the center of the screen can be performed. However, during surgery, when a blood vessel is pinched by a clip applier, a visual field operation such as confirming that the tip of the clip applier is properly pinching the blood vessel may be required. In this case, it is necessary to look into the observation target from different angles, but in order to perform such an operation, it is necessary to perform a precise visual field operation in consideration of the distance and position information between the distal end of the endoscope and the observation target.

FIG. 12 is a diagram showing an example of the positional relationship between the endoscope and the observation target in the patient's body. In the example of this figure, when a blood vessel 101 is sandwiched between clip appliers 102, it is confirmed by an endoscope 10 whether the tip of the clip applier 102 properly sandwiches the blood vessel 101. The vicinity of the tip of the clip applier 102 is an observation target 103. The endoscope 10 is composed of a long insertion shaft 11, a distal end portion 12, and a curved portion 13 between the insertion shaft 11 and the distal end portion 12.

At the time of insertion into the body, the endoscope 10 is inserted in a straightened state as shown by A in the figure. Then, at the time of observation, the endoscope 10 is curved by changing the angle of the curved portion 13, so that the distal end of the endoscope faces the observation target 103. At this time, it is necessary to consider the distance between the distal end of the endoscope and the observation target 103 (the positional relationship between the endoscope 10 and the observation target 103). If only the insertion shaft 11 is simply tilted, the position of the endoscope 10 will be as shown in C in the figure, and the distance from the distal end of the endoscope to the observation target 103 is long, so that the observation target 103 cannot be seen. As shown in B in the figure, in a case where the distance from the distal end of the endoscope to the observation target 103 is short, the observation target 103 can be seen.

As a method of obtaining distance and position information, a method of providing a distance-measuring sensor at the distal end of the endoscope can be considered. However, this method has problems such as a large insertion diameter of the endoscope and a limited number of sensors that can be sterilized and disinfected and can be brought into the body cavity. Therefore, a method of obtaining distance and position information without inserting a sensor into the body cavity is desirable. As such a method, for example, Japanese Patent (Granted) Publication No. 6091410 (hereinafter referred to as Patent Document 2) discloses an endoscopic system in which two images are captured by bending a curved portion on the distal end side of the endoscope by a predetermined angle, and the distance from those images to the observation target is measured.

In the endoscope system disclosed in Patent Document 2, two images are captured by changing the angle of the curved portion, and the distance from the distal end of the endoscope to the observation target is calculated based on the images. Therefore, it is possible to measure the distance in the body cavity without providing a special sensor. However, the position of the observation target on the image moves by changing the angle of the curved portion when measuring the distance. Alternatively, the image after the angle change may be displayed so that the position of the observation target on the image does not move, but in this case, there is a time when the current situation is not displayed. Therefore, the concentration of the operator is hindered. In addition, if the observation target moves during distance measurement, there is a problem in that distance measurement cannot be performed accurately.

When changing the angle of the curved portion in order to capture a second image, there is also a method of displaying the image before changing the angle on the screen while changing the angle. However, it is synonymous with not observing the surgical site during that time, and a method in surgery that requires constant attention to the surgical site is not desirable.

SUMMARY

Embodiments of the present invention provide an endoscopic distance-measuring method and an endoscopic system capable of calculating the distance from the observation target and performing the procedure with the optimum field of view without disturbing the concentration of the operator, by using visual feedback control to maintain a state in which the position of the observation target is captured even when the endoscope is curved.

A distance-measuring method measures a distance from a distal end portion of an endoscope to an observation target in a state in which the endoscope is inserted into a body cavity via a trocar, the endoscope including the distal end portion having an imaging portion and an elongated portion having a curved portion. The distance-measuring method includes: acquiring a first curvature angle of the curved portion in a first state in which the endoscope is inserted into the body cavity and captures the observation target; acquiring a second curvature angle of the curved portion in a second state in which an insertion direction of the endoscope is changed with a position of the trocar as a pivot point while capturing the same observation target as in the first state; acquiring a change amount in an insertion angle due to a change in the insertion direction; acquiring an insertion amount of the endoscope from the pivot point of the trocar to the curved portion; and calculating a distance (D) between the distal end portion and the observation target, based on the first curvature angle, the second curvature angle ($\beta$), the change amount ($\alpha$) in the insertion angle, the insertion amount (c), and a length (d) of the distal end portion.

The distance-measuring method may further include: defining a polygon using the first curvature angle, the second curvature angle, the change amount in the insertion angle, the insertion amount, and the length of the distal end portion; and calculating the distance between the distal end portion and the observation target based on the polygon.

The polygon may be a triangle having the observation target as one of apexes.

The distance-measuring method may further include: calculating an angle of the apex of the triangle where the observation target is located, based on change amounts in the first curvature angle, the second curvature angle, and the insertion angle.

The distance-measuring method may further include: calculating an angle (s) formed by a straight line extending the imaging portion to the observation target in the first state and a straight line extending the imaging portion to the observation target in the second state, based on change amounts in the first curvature angle, the second curvature angle, and the insertion angle; and calculating the distance to the observation target.

An endoscope system includes an endoscope having a distal end portion having an imaging portion and an elongated portion having a curved portion, and a controller. In order to measure a distance from a distal end portion to an observation target when the endoscope is inserted into a body cavity via a trocar, the controller acquires a first curvature angle of the curved portion in a first state in which the endoscope is inserted into the body cavity and captures the observation target, a second curvature angle of the curved portion in the second state in which an insertion direction of the endoscope is changed with a position of the trocar as a pivot point while capturing the same observation target as in the first state, a change amount in an insertion angle due to a change in the insertion direction, and an insertion amount of the endoscope from the pivot point of the trocar to the curved portion, and calculates a distance (D) between the distal end portion and the observation target, based on the first curvature angle, the second curvature angle ($\theta$), a change amount (a) in the insertion angle, the insertion amount (c), and a length (d) of the distal end portion.

The controller may define a polygon using the first curvature angle, the second curvature angle, the change amount in the insertion angle, the insertion amount, and the length of the distal end portion, and calculate the distance between the distal end portion and the observation target based on the polygon.

The polygon may be a triangle having the observation target as one of apexes.

The controller may calculate an angle of the apex of the triangle where the observation target is located based on change amounts in the first curvature angle, the second curvature angle, and the insertion angle.

The controller may calculate the angle (s) formed by a straight line extending the imaging portion to the observation target in the first state and a straight line extending the imaging portion to the observation target in the second state, based on change amounts in the first curvature angle, the second curvature angle, and the insertion angle, and calculate the distance to the observation target.

The controller may calculate a result of statistical processing from a plurality of distances calculated by repeating a series of processes a plurality of times as the distance.

The controller may calculate the distance when an operation input by an operator is not performed for a predetermined time or more.

According to the endoscopic distance-measuring method and the endoscope system in accordance with embodiments of the present invention, the distance to the target can be calculated and the procedure can be performed with the optimum field of view without disturbing the concentration of the operator, by using visual feedback control to maintain a state in which the target position is captured even when the endoscope is curved.

DETAILED DESCRIPTION OF THE PREFERRED EMBODIMENT

Figure 1:
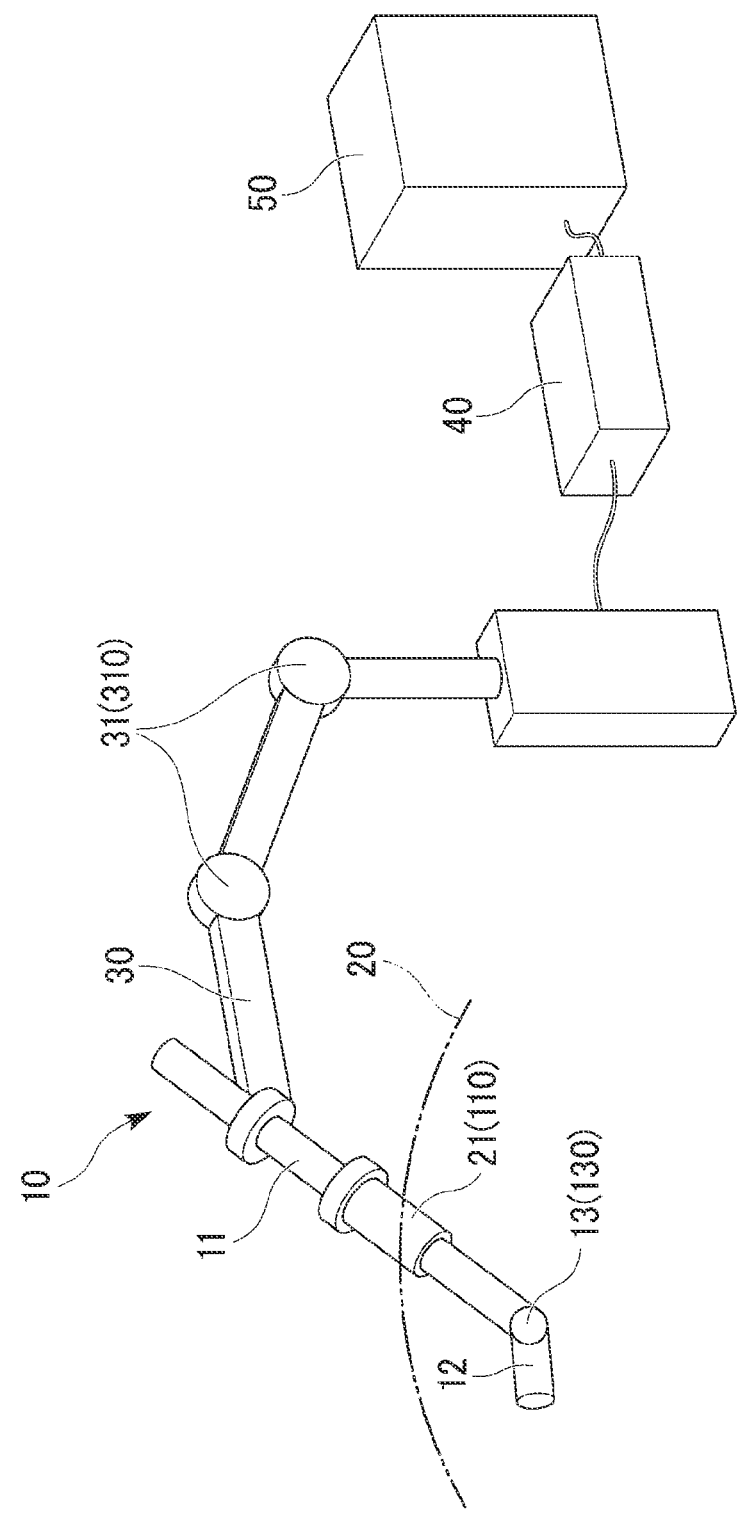
FIG. 1 is a diagram showing an overall configuration of an endoscope system according to an embodiment of the present invention.

An embodiment of the endoscope system of the present invention will be described with reference to the drawings. FIG. 1 is a diagram showing an overall configuration of an endoscope system according to the embodiment of the present invention. The endoscope system has an endoscope 10 that observes (images) the inside of a patient's body cavity. The endoscope 10 is composed of a long insertion shaft (elongated portion) 11, a distal end portion 12, and a curved portion 13 located between the elongated portion 11 and the distal end portion 12. The distal end portion 12 is located at the distal end of the endoscope 10 and has an imaging portion.

The curved portion 13 is located on the distal end side of the endoscope 10, and the distal end portion 12 is curved from the elongated portion 11 by a predetermined angle (distal end curvature angle). The curved portion 13 has a curved state-detecting means 130 that detects a curved state (distal end curvature angle) in which the distal end portion 12 is curved from the elongated portion 11.

The elongated portion 11 is inserted (introduced) into the body cavity during the operation, for example, through the trocar 21 punctured into the abdominal wall 20 of the patient (inserted into the trocar 21). The elongated portion 11 or the trocar 21 has an insertion amount-detecting means 110 that detects the insertion amount inserted into the body cavity by the endoscope 10 (elongated portion 11).

The elongated portion 11 is held by the arm 30. The arm 30 holds the proximal end side of the endoscope 10 and has a joint mechanism 31 that changes the position or orientation of the endoscope 10. The joint mechanism 31 includes a flexion state-detecting means 310 that detects the flexion state of the joint mechanism 31. The endoscope 10 and the arm 30 are controlled by a controller 40 provided in the system 50.

Figure 2:
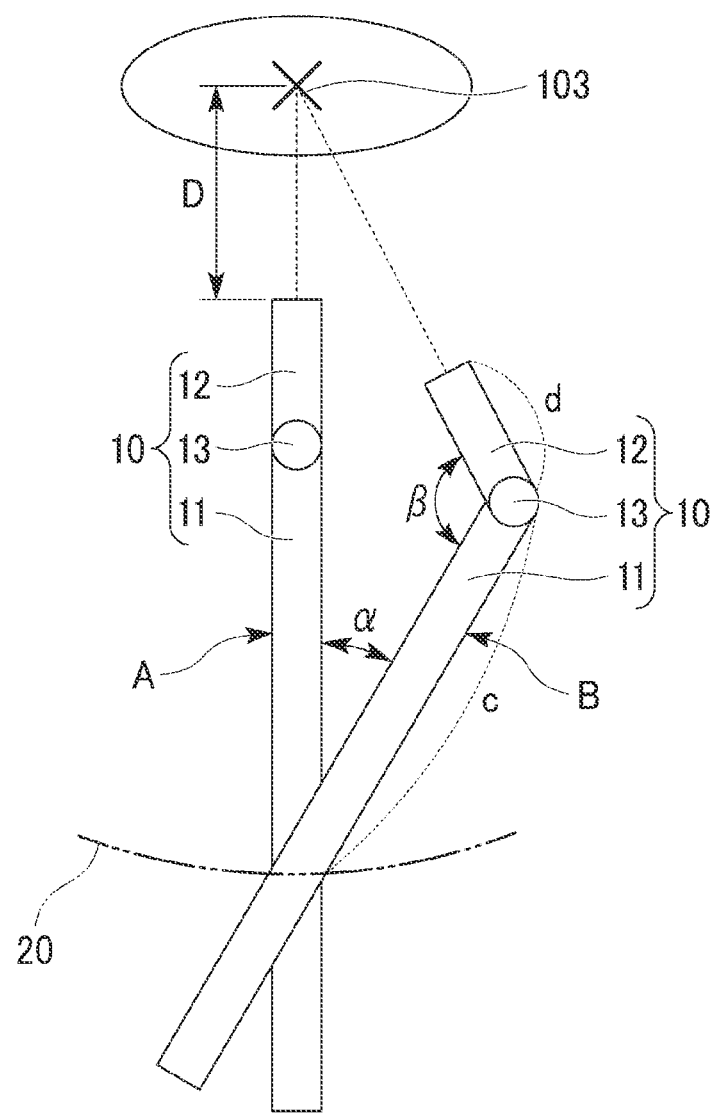
FIG. 2 is a diagram showing an example of a positional relationship between an endoscope and an observation target in a patient's body in the endoscope system according to the embodiment of the present invention.

FIG. 2 is a diagram showing an example of the positional relationship between the endoscope and the observation target in the patient's body in the endoscope system according to the present embodiment. It is desired to measure the distance D from the distal end of the endoscope to the observation target 103 in the body cavity. Therefore, in the present embodiment, the observation target 103 is continuously captured in an arbitrary area on the screen (for example, the center of the screen) by the visual feedback control, and the endoscope 10 is operated in this state to change the operating angle (pivot angle) and the distal end curvature angle of the endoscope (from state A to state B in FIG. 2). The distance between the distal end of the endoscope and the observation target 103 is calculated based on the operation amount of the endoscope 10 (operation angle, distal end curvature angle, endoscope insertion amount, etc.) at this time.

At the time of insertion into the body, the endoscope 10 is inserted in a straightened state as shown by A in FIG. 2 (first state). Then, with the distal end of the endoscope facing the observation target 103, the endoscope 10 is curved by changing the angle of the curved portion 13 as shown in B in FIG. 2 (second state).

As shown in FIG. 2, the operating angle of the endoscope is an angle α formed by the elongated portion 11 in the first state and the elongated portion 11 in the second state. The operating angle of the endoscope can be calculated from the flexed state of the joint mechanism 31 detected by the flexion state-detecting means 310. The curvature angle of the endoscope is the angle R formed by the elongated portion 11 and the distal end portion 12 in the second state. The insertion amount of the endoscope is the length c from the abdominal wall 20 to the curved portion 13 in the second state. The length d of the distal end portion 12 of the endoscope (the length of the distal end hard portion) is a known parameter. The specific calculation method of distance measurement will be described later.

The controller 40 includes a control means and a distance-measuring means. The controller 40 (control means) monitors the movement amount of the observation target on the screen by visual feedback control, and controls the distal end curvature angle of the endoscope 10 so as to keep the observation target 103 at an arbitrary position on the screen. Since the control means keeps the observation target 103 at an arbitrary position on the screen, the concentration of the operator is not hindered The controller 40 (distance-measuring means) calculates the distance between the distal end of the endoscope and the observation target 103, based on the distal end curvature angle of the endoscope, the operation amount of the endoscope (operation angle, insertion amount), and the parameters of the endoscope (the length of the distal end hard portion) in a first state (A in the figure) in which the observation target 103 is captured at an arbitrary position (for example, the center position) and a second state (B in the figure) in which the observation target 103 is driven by a predetermined operation amount while being captured at an arbitrary position. With the distance-measuring means, it is possible to measure the distance in the body cavity without providing a sensor at the distal end of the endoscope.

Specifically, the distance is measured as follows. First, in the first state in which the endoscope 10 captures the observation target 103 at an arbitrary position (for example, the center position), the controller 40 acquires the first curved state from the curved state-detecting means 130. Further, the controller 40 acquires the first flexion state from the flexion state-detecting means 310. Further, the controller 40 acquires the first insertion amount from the insertion amount-detecting means 110.

Then, in order to operate the joint mechanism 31 and the curved portion 13 so that the elongated portion 11 forms a predetermined angle in a predetermined direction before and after the movement, the controller 40 generates a control signal by visual feedback control from the image captured by the imaging portion at the distal end of the endoscope. The controller 40 operates the joint mechanism 31 and the curved portion 13 by the control signal, and sets to the second state in which the observation target 103 is driven by a predetermined operation amount while being captured at an arbitrary position.

In the second state, the controller 40 acquires a second curved state from the curved state-detecting means 130. Further, a second flexion state is acquired from the flexion state-detecting means 310. In addition, a second insertion amount is acquired from the insertion amount-detecting means 110.

Then, the controller 40 calculates the distance between the imaging portion (distal end of the endoscope) and the predetermined area (observation target 103) from the acquired first curved state, first flexion state, first insertion amount, second curved state, second flexion state and second insertion amount.

In this way, since the distance is calculated from the movement amount (operating angle, curvature angle, insertion amount) of the endoscope, it is not necessary to provide a special sensor at the distal end of the endoscope. Since the distance is measured while the observation target 103 is continuously captured at an arbitrary position on the screen by the visual feedback control, the concentration of the operator is not hindered.

The system may also include distance measurement error determination means. The distance measurement error determination means monitors the movement amount of the observation target 103 and the movement amount of the endoscope 10 on the screen, and determines that the distance measurement result is incorrect when the movement amount of the observation target 103 deviates from a predetermined condition with respect to the movement amount of the endoscope 10. When the object moves, the distance measurement error determination means determines that the distance measurement is an error, so that an erroneous distance measurement result can be prevented. Further, when the observation target 103 moves, the distance measurement can be stopped. The operation of the distance measurement error determination means will be described later.

Figure 3A:
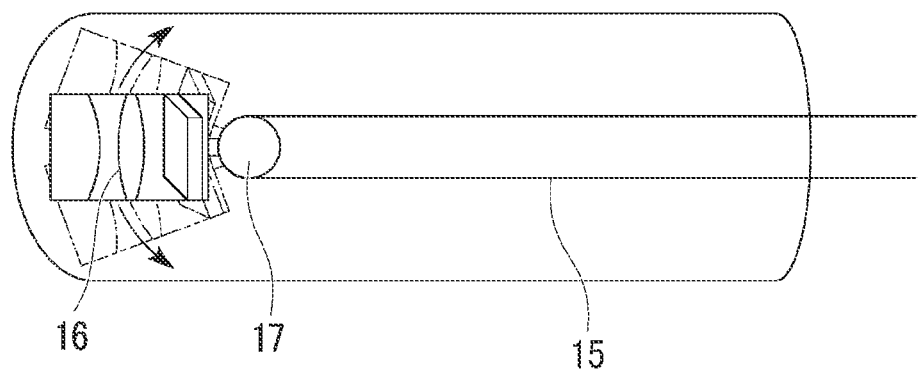
FIG. 3A is a diagram showing an example of an endoscope having a curved portion at the distal end.
Figure 3B:
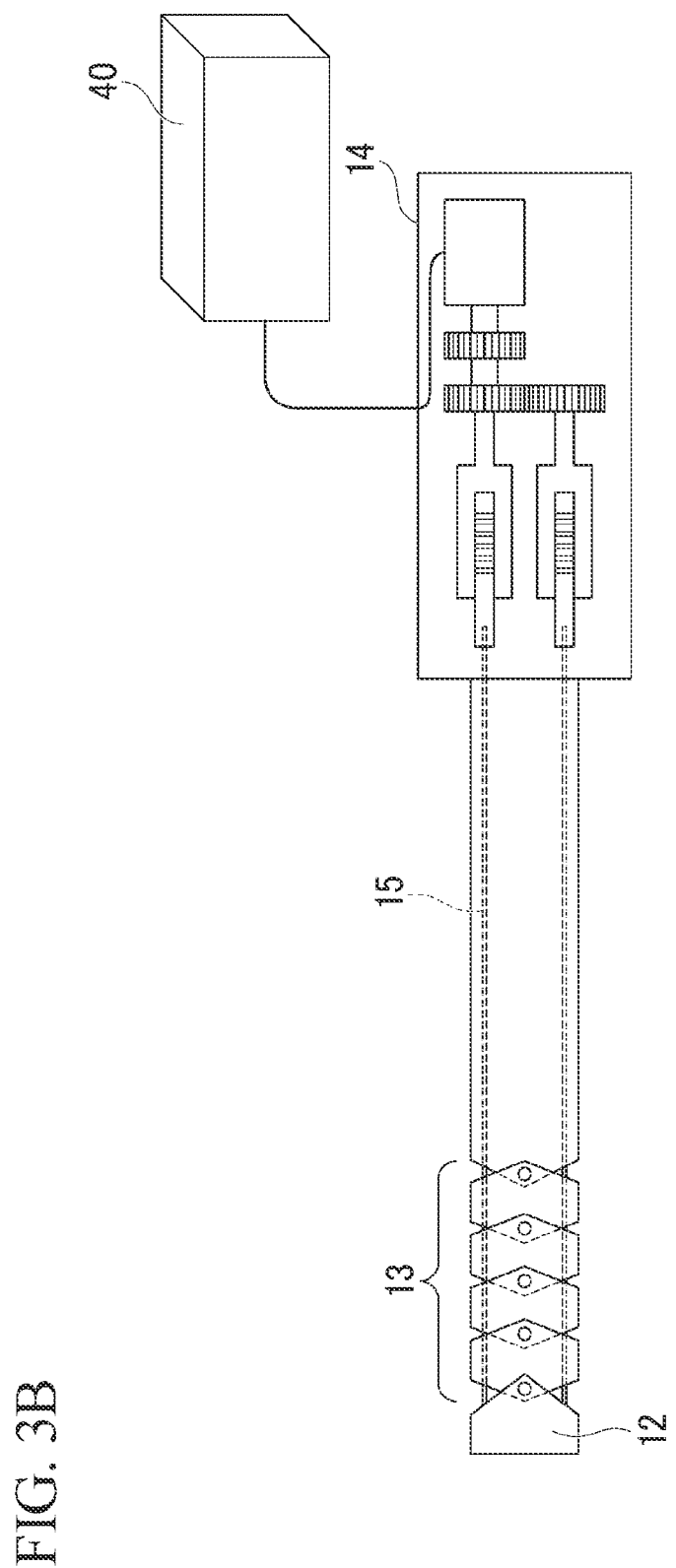
FIG. 3B is a diagram showing an example of an endoscope having a curved portion at the distal end.

FIGS. 3A and 3B are views showing an example of an endoscope having a curved portion at the distal end. The endoscope shown in FIG. 3B has an electric drive portion 14 (motor, etc.) and can drive a curved portion 13 on the distal end side of the endoscope via a power transmission portion 15 (wire, shaft, etc.). The drive portion 14 is driven by receiving a command from the control portion (controller 40).

FIG. 3A is an example in which the curved portion 13 (optical axis direction-changing means) is configured by driving the optical system 16 of the endoscope. The drive portion 14 rotationally drives the optical system 16 including the imaging element with the rotation shaft 17 as an axis via the power transmission portion 15. By changing the orientation of the optical system 16 in this way, the orientation of the imaging portion at the distal end of the endoscope can be changed. In the present embodiment, it is assumed that the curved portion includes an optical axis direction-changing means having a configuration for changing the direction of the optical axis as shown in FIG. 3A.

The drive portion 14 is provided with a sensor (curvature angle-detecting means) such as an encoder, and the drive amount of the power transmission portion 15 can be grasped from the sensor output, and the curvature angle of the curved portion 13 can be calculated.

Figure 4:
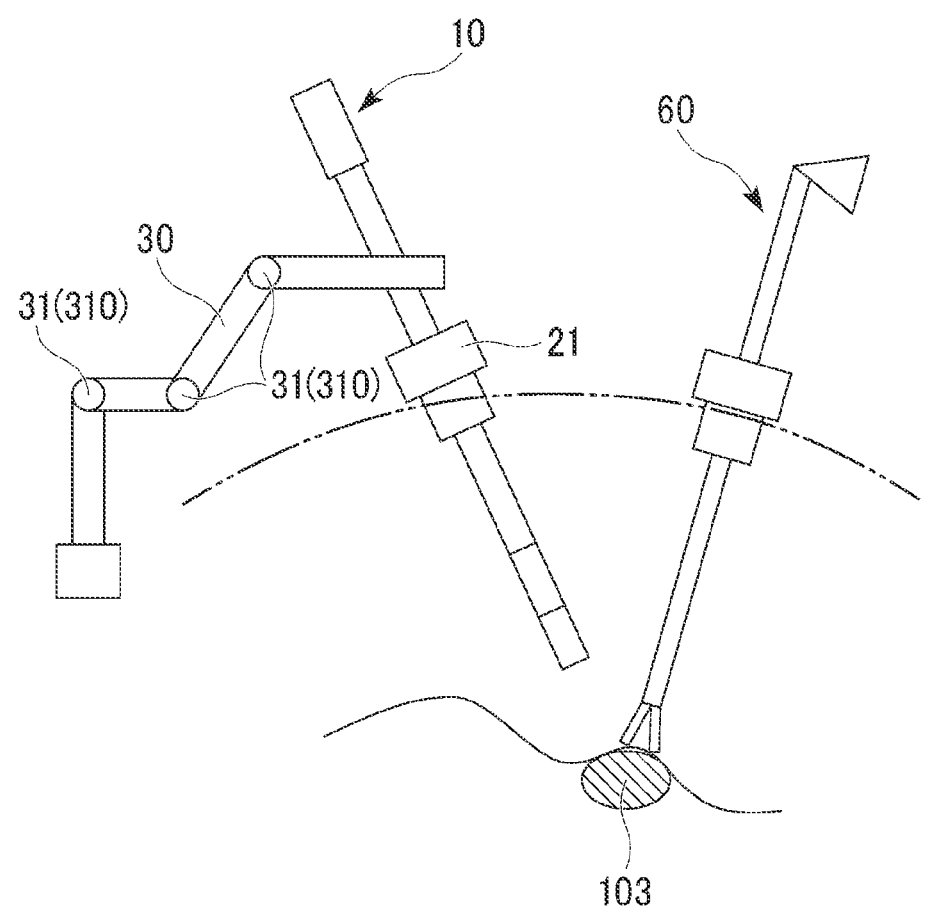
FIG. 4 is a diagram showing a state in which a procedure is performed using the endoscope according to the embodiment of the present invention.
Figure 5:
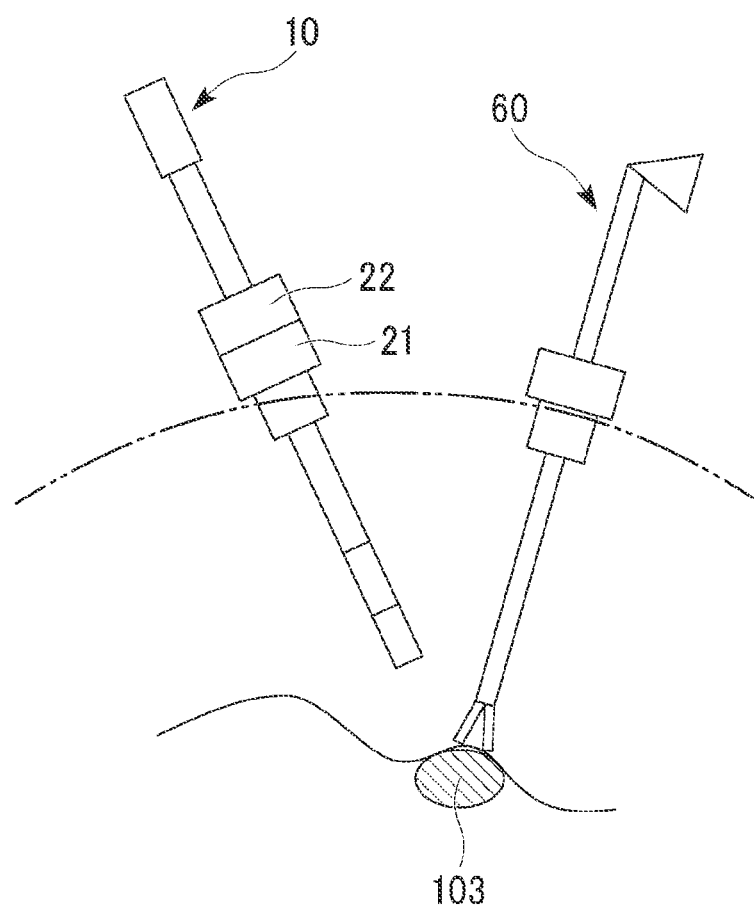
FIG. 5 is a diagram showing a state in which a procedure is performed using the endoscope according to the embodiment of the present invention.

FIGS. 4 and 5 are views showing how the procedure is performed using the endoscope 10 and the treatment tool 60 according to the present embodiment. In the example of FIG. 4, in the arm 30 having a plurality of joints holding the endoscope 10, each joint of the arm 30 is provided with a sensor (operation angle-detecting means, insertion amount-detecting means), and can measure the angle of each joint. Then, from the angle of each joint, it is possible to calculate how much the endoscope is tilted and the operating angle. In addition, the insertion amount can be calculated from the angle of each joint to determine how much the endoscope has been inserted.

When operating the endoscope by hand without using an arm, for example, the present invention can be performed in the same manner by acquiring the pivot information of the endoscope by a pivot-detecting means.

In the example of FIG. 5, the endoscope 10 is inserted into the body cavity via the trocar 21, but the first sensor 22 is attached to the trocar 21. The first sensor 22 (operation angle-detecting means) attached to the trocar 21 can measure the orientation of an orientation sensor or the like. Therefore, the operating angle can be detected by the first sensor 22 as to how much the endoscope 10 is tilted. Specifically, the first sensor 22 detects an operation angle with the position of the trocar 21 in the elongated portion of the endoscope 10 as a pivot point. Further, the second sensor 23 (insertion amount-detecting means) attached to the trocar 21 is an optical sensor or the like, and can detect the insertion amount.

A known technique can be used for the visual feedback control by the control means (controller 40). The image-processing portion included in the control means tracks the observation target 103 on the image by using an image-matching technique such as template matching. Then, the control means feeds back the position of the tracked observation target 103 on the screen, and controls the curved portion 12 of the endoscope so that the observation target 103 comes to an arbitrary position on the screen. As a result, it is possible to control so that the designated observation target 103 on the image is continuously captured at an arbitrary position on the screen.

Figure 6:
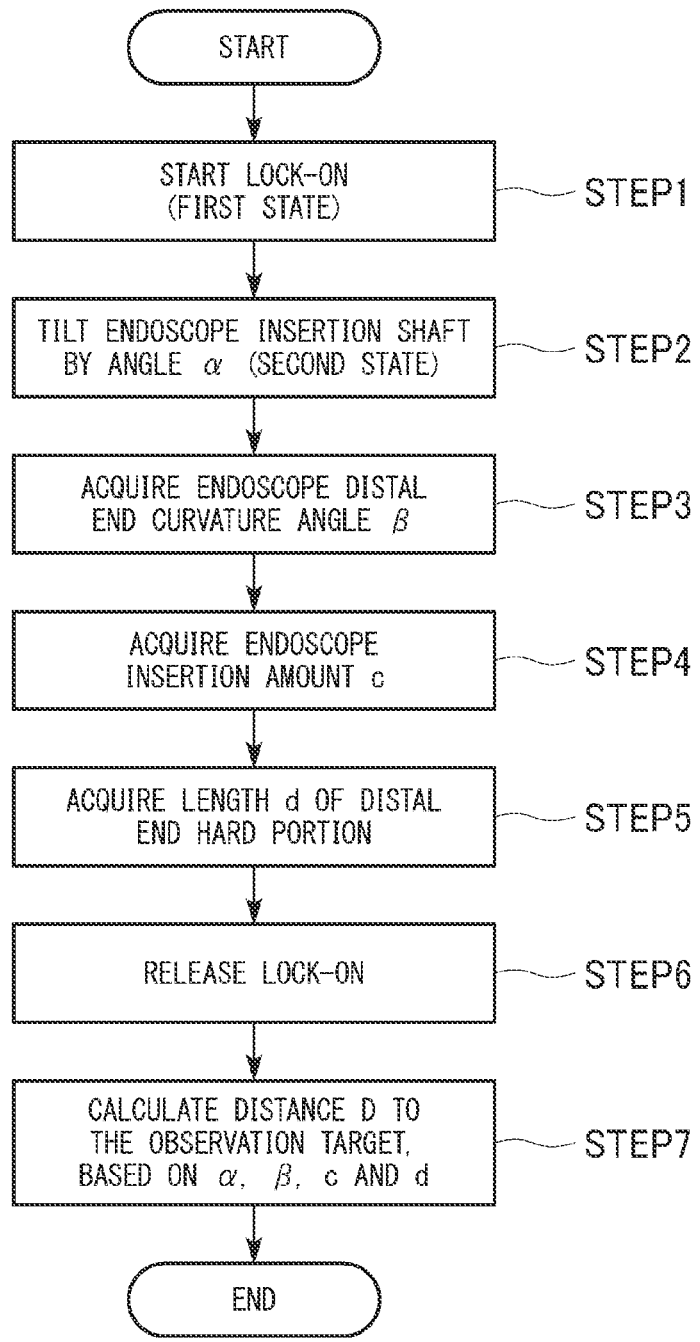
FIG. 6 is a flowchart showing a procedure of a distance-measuring method using the endoscope according to the embodiment of the present invention.

FIG. 6 is a flowchart showing the procedure of the distance-measuring method by the distance-measuring means (controller 40). The distance-measuring step by the distance-measuring means is performed by the procedure of FIG. 6.

(Step 1)

The control means keeps capturing the observation target at an arbitrary position (predetermined area) on the screen by visual feedback control (first state). That is, the lock-on that captures the observation target in a predetermined area on the screen is started.

(Step 2)

Next, as shown in FIG. 2, only the insertion shaft (elongated portion) 11 of the endoscope 10 is tilted by a predetermined angle α by the arm 30 or the operator's hand.

(Step 3)

Then, the curved portion 13 of the endoscope 10 becomes an angle R (due to lock-on) so as to continue to capture the observation target (second state). The distance-measuring means acquires an angle R (endoscope distal end curvature angle).

(Step 4)

In this state (second state), the distance-measuring means acquires the endoscope insertion amount c.

(Step 5)

Then, the distance-measuring means acquires the length d of the distal end hard portion. However, the length d of the hard portion at the distal end of the endoscope is a specified value (known).

(Step 6)

After that, the control means releases the lock-on. Note that this step 6 may be before or after step 7.

(Step 7)

The distance-measuring means calculates the distance D between the distal end of the endoscope and the observation target, based on the obtained operating angle α, the curvature angle R, the insertion amount c of the endoscope, and the length d of the distal end of the known endoscope.

Figure 7:
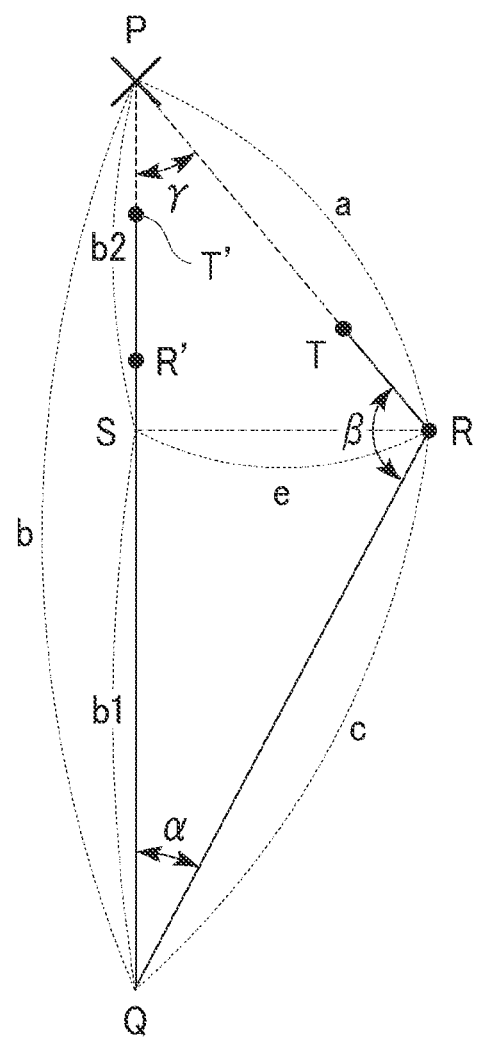
FIG. 7 is a diagram showing an example of the positional relationship between the endoscope and the observation target of the endoscope according to the embodiment of the present invention.

The calculation method of the distance D will be described. FIG. 7 is a diagram showing the positional relationship between the endoscope and the observation target when the initial state (first state) of the endoscope is straight. The point P indicates the position of the observation target 103. The point Q indicates the position where the endoscope is inserted into the body cavity, and does not change between the first state and the second state. The point R indicates the position of the curved portion 13 in the second state. The point S is the foot of the perpendicular line drawn from R to the straight line PQ. The endoscope in the first state is located on the straight line PQ. The point R' indicates the position of the curved portion 13 in the first state. Further, the endoscope in the second state is located on the polygonal line PRQ. The point T' indicates the position of the distal end of the endoscope in the first state. The point T indicates the position of the distal end of the endoscope in the second state. In FIG. 7, the portion where the endoscope is actually located is drawn with a solid line.

As shown in FIG. 7, assuming that PR=a, PQ=b, QR=c, RS=e, QS=b1, PS=b2, angle PQR=α, angle PRQ=β, angle QPR=γ, by the law of cosines, $\cos\alpha=(b^2+c^2-a^2)/2bc$, $\cos\beta=(a^2+c^2-b^2)/2ac$, and $\cos\gamma=(a^2+b^2-c^2)/2ab$ are established.

Since $e=c\times\sin\alpha$ and $e=b2\times\tan\gamma$ are established, $b2=e/\tan\gamma=c\times\sin\alpha/\tan\gamma$, and b2 can be obtained from c, α, and γ. Further, since $b1=c\times\cos\alpha$ and $b=b1+b2$ are established, b (=PQ) can be obtained. Then, since b=PQ=PT'+T'R'+R'Q=D+d+c is established, the distance D between the distal end of the endoscope and the observation target can be calculated from D=b−c−d.

Figure 8A:
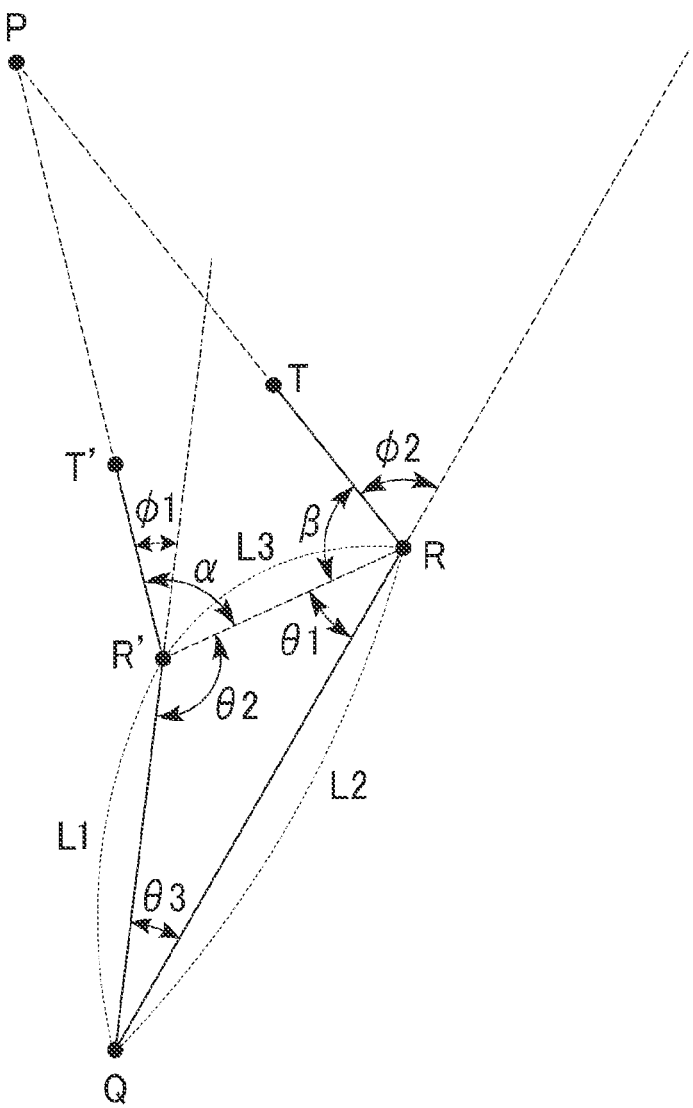
FIG. 8A is a diagram showing another example of the positional relationship between the endoscope and the observation target of the endoscope according to the embodiment of the present invention.
Figure 8B:
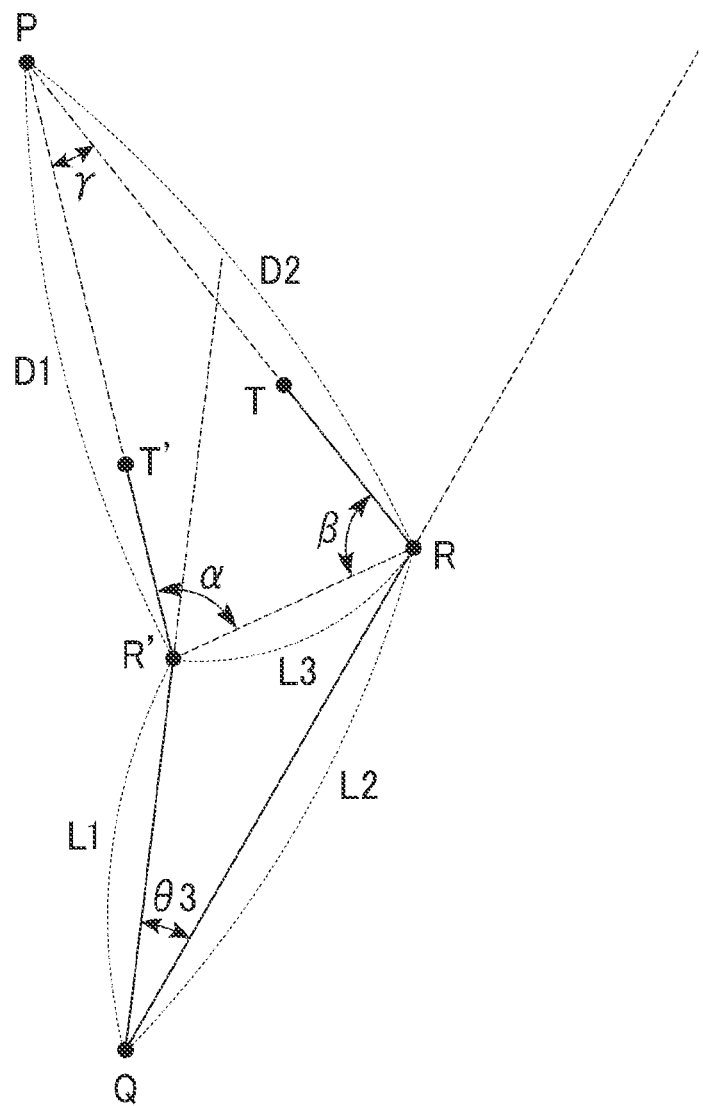
FIG. 8B is a diagram showing another example of the positional relationship between the endoscope and the observation target of the endoscope according to the embodiment of the present invention.

The distance D can be calculated in the same manner when the initial state (first state) of the endoscope is curved. FIGS. 8A and 8B are diagrams showing the positional relationship between the endoscope and the observation target when the initial state (first state) of the endoscope is curved. The point P indicates the position of the observation target 103. The point Q indicates the position where the endoscope is inserted into the body cavity, and does not change between the first state and the second state. The point R' indicates the position of the curved portion 13 in the first state. The point R indicates the position of the curved portion 13 in the second state. The point T' indicates the position of the distal end of the endoscope in the first state. The point T indicates the position of the distal end of the endoscope in the second state. In FIGS. 8A and 8B, the portion where the endoscope is actually located is drawn with a solid line.

As shown in FIG. 8A, the curvature angle Φ1 of the curved portion in the first state, the curvature angle Φ2 of the curved portion in the second state, and the operating angle of the endoscope (the amount of change from the first state to the second state, the angle RQR') θ3 can be measured. QR'=L1 and QR=L2 can be obtained from the insertion amount of the endoscope. Therefore, assuming that RR'=L3, angle QRR'=θ1, and angle QR'R=θ2, L3, θ1, and θ2 can be obtained from the law of cosines.

As shown in FIG. 8B, assuming that the angle PR'R=α, the angle PRR'=β, and the angle RPR'=γ, then $\alpha-\varphi1+\theta2=\pi$ and $\beta+\varphi2+\theta1=\pi$ are established, so $\alpha=\pi+\varphi1-\theta2$, $\beta=\pi-\Phi2-\theta1$, $\gamma=\pi-\alpha-\beta=\pi-\Phi1+\Phi2+\theta1+\theta2$. Assuming that PR'=D1 and PR=D2, $D1/\sin\beta=L3/\sin\gamma$ and $D2/\sin\alpha=L3/\sin\gamma$ are established from the law of sines. Therefore, $D1=L3\times\sin\beta/\sin\gamma$ and $D2=L3\times\sin\alpha/\sin\gamma$, and D1 and D2 can be obtained. Therefore, the distance D between the distal end of the endoscope and the observation target can be calculated from this.

Next, the operation of the distance measurement error determination means will be described. The movement amount of the observation target 103 on the image is calculated from the change amount of position on the screen by tracking it by the image-processing portion using an image-matching technique such as template matching. The movement amount (operating angle, curvature angle, insertion amount) of the endoscope 10 is calculated by the curvature angle-detecting means, the operating angle-detecting means, and the operation amount-detecting means.

The distance measurement error determination means compares the movement amount of the observation target 103 with the movement amount of the endoscope 10 during the distance-measuring operation (when the observation target is captured in the center of the screen), and when the movement amount of the observation target 103 deviates from the predetermined condition with respect to the movement amount of the endoscope 10 (for example, when it is larger than the predetermined threshold value), it is determined that the observation target 103 has moved. The predetermined condition (threshold value) is set based on the required distance measurement accuracy, the operation accuracy of the endoscope 10, and the like. This case includes the case when the observation target 103 operates even though the endoscope 10 is not operating, the case when the movement direction of the observation target 103 is opposite to the direction predicted from the operation of the endoscope 10, and the case when the direction predicted from the movement of the endoscope 10 and the movement direction of the observation target 103 are the same but move significantly beyond the threshold value.

Figure 9A:
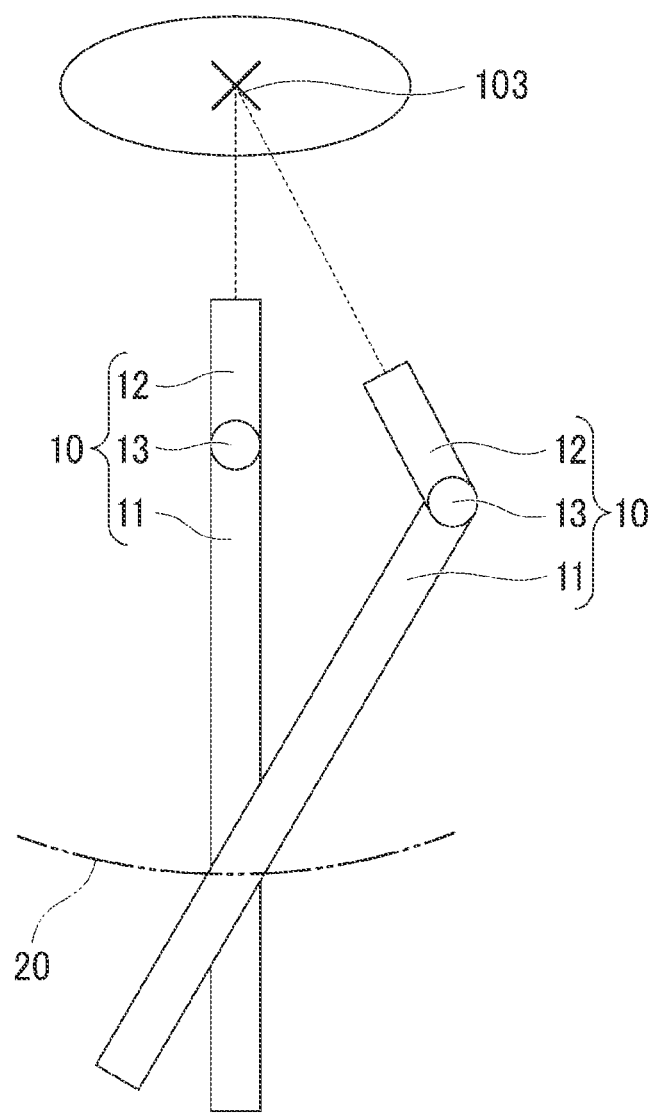
FIG. 9A is a diagram showing a case where the movement amount of the observation target satisfies a predetermined condition with respect to the movement amount of the endoscope in the endoscope according to the embodiment of the present invention.
Figure 9B:
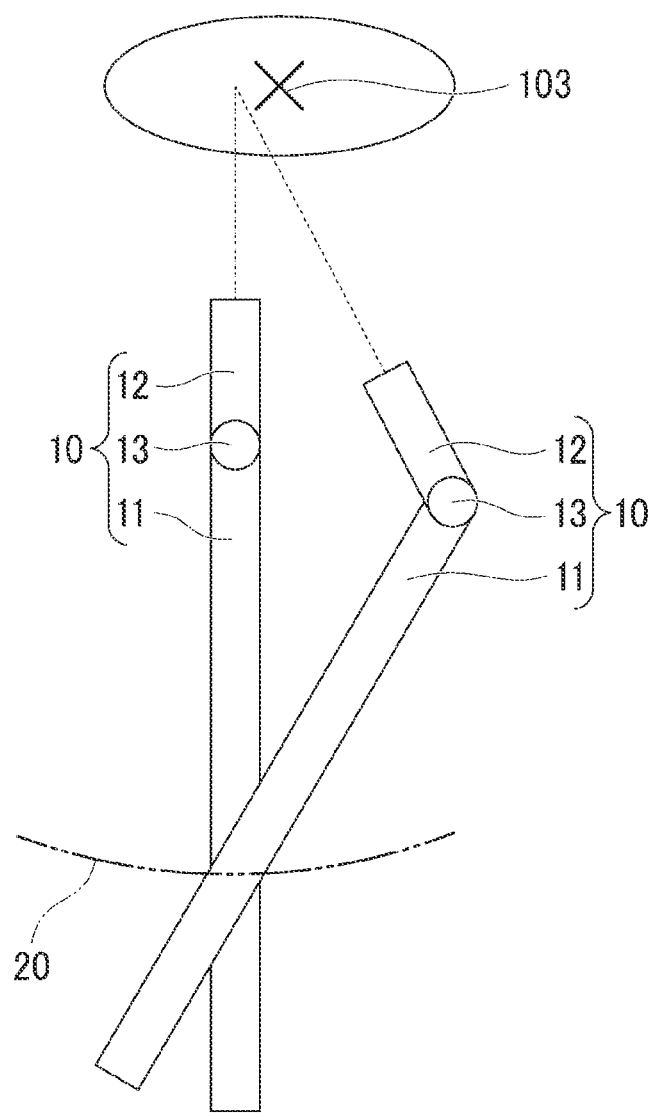
FIG. 9B is a diagram showing a case where the movement amount of the observation target deviates from a predetermined condition with respect to the movement amount of the endoscope in the endoscope according to the embodiment of the present invention.

FIG. 9A is a diagram showing a case where the movement amount of the observation target 103 satisfies a predetermined condition with respect to the movement amount of the endoscope 10, and FIG. 9B is a diagram showing a case where the movement amount of the observation target 103 deviates from a predetermined condition with respect to the movement amount of the endoscope 10.

When the distance measurement error determination means determines that the observation target 103 has moved, the distance-measuring result is regarded as an error, and the distance-measuring result is invalidated. Further, the distance measurement error determination means may notify the user by displaying on the screen that the distance measurement has failed. In this way, when the object moves during distance measurement by the distance measurement error determination means, it can be determined that the distance measurement result is incorrect.

The timing at which the distance-measuring means (controller 40) performs (starts) the distance-measuring step may be instructed by the distance-measuring instruction means provided in the system. In this case, the operator (surgeon, assistant, or the like) instructs the distance measurement using the distance-measuring instruction means. The distance-measuring means performs distance measuring at the timing instructed by the distance-measuring instruction means. By this method, the distance measurement can be performed at any timing by the operator. The distance-measuring instruction means may be a known means such as a switch or voice.

Regarding the timing at which the distance-measuring means (controller 40) performs (starts) the distance-measuring step, the system may automatically perform the distance measuring at the timing when the operator is interrupting the operation. That is, if the operation input by the operator is not made for a predetermined time or more, the mode may shift to the distance-measuring mode in which the distance-measuring step is performed. In the distance-measuring mode, the distance between the imaging portion and the observation target is calculated by operating the endoscope and the arm in a predetermined manner. In this case, the system determines the interruption of the ranging mode (distance-measuring step) based on the information of the image, the sensor that captures the movement of the operator, the camera, and the like. According to this method, distance measurement can be automatically performed at a timing that does not interfere with the concentration of the operator.

The system may automatically determine the timing at which the distance-measuring means (controller 40) performs (starts) the distance-measuring step based on the imaging scene. That is, the distance may be measured before the operator is using the endoscope.

As a method of improving the accuracy of distance measurement, that is, improving the measurement accuracy, the endoscope is moved in multiple directions to measure the distance multiple times, and the measurement accuracy can be improved by excluding the values that deviate significantly from those measurement results or by taking the average value. That is, the result of statistical processing from a plurality of distances calculated by repeating a series of processes a plurality of times may be calculated as a distance.

Figure 10:
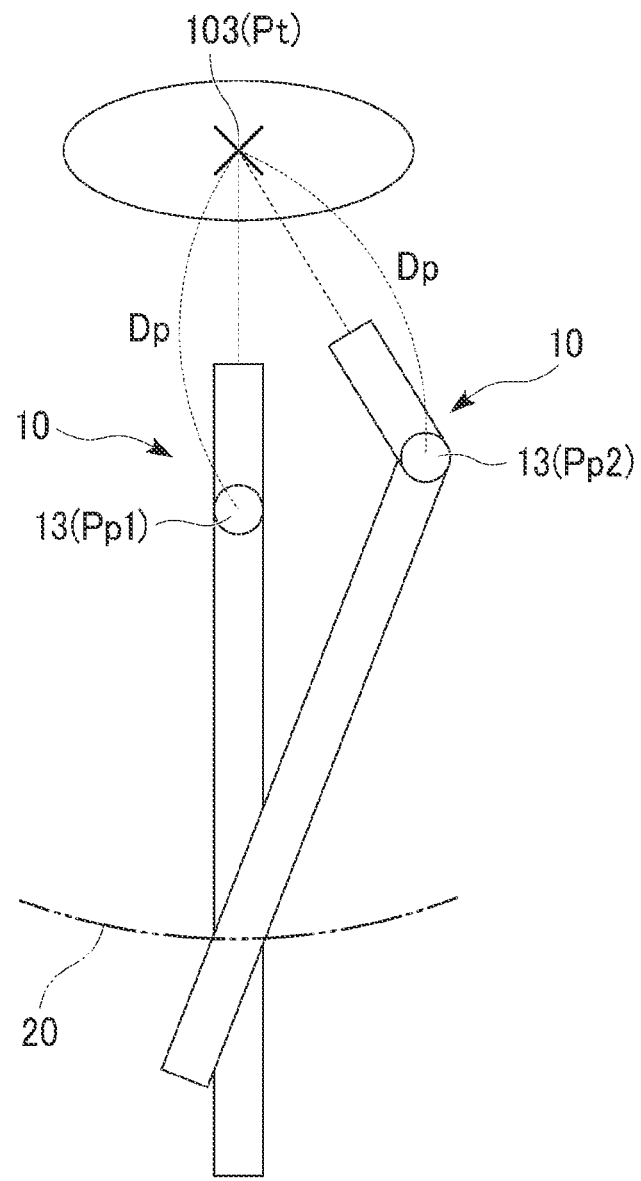
FIG. 10 is a diagram showing a positional relationship between a curved portion and the observation target of the endoscope according to the embodiment of the present invention.

As a usage mode of the distance measurement result (distance measurement information), an example in which visual feedback control and distance measurement information are combined can be considered. FIG. 10 is a diagram showing the positional relationship between the curved portion 13 of the endoscope 10 and the observation target 103 according to the present embodiment. In FIG. 10, the position of the observation target 103 is Pt, the root position of the curved portion 13 in the first state is Pp1, and the root position of the curved portion 13 in the second state is Pp2.

After calculating the distance (distance measurement information) between the distal end of the endoscope and the observation target by visual feedback control, the mode shifts to the position control mode so that the distance between the distal end of the endoscope and the observation target becomes a constant value. As shown in FIG. 10, the position is controlled so that the distance between Pt and Pp1 and the distance between Pt and Pp2 have a constant value Dp. In this state (mode), the operator can perform the observation and the procedure while maintaining the distance between the distal end of the endoscope and the observation target.

The position (three-dimensional coordinates) Pt of the observation target 103 can be specified from the distance measurement information. Further, if the endoscope 10 is held by an arm (a sensor is provided in each joint) or the like, the root position Pp (Pp1, Pp2) of the curved portion can be known. Specifically, Pt and Pp can be obtained by calculating the kinematics of the arm and the endoscope with distance information added.

When it is desired to observe the observation target 103 from a desired angle, the root position Pp of the curved portion is moved to a desired position with respect to the position Pt of the observation target 103. At that time, at the same time, the angle of the curved portion 13 of the endoscope 10 is controlled by visual feedback control so that the position of the observation target on the screen comes to a predetermined region such as the center of the screen. Then, if the position is controlled so that the distance between Pt and Pp1 and the distance between Pt and Pp2 become a constant value Dp, the observation target can be observed from different angles while maintaining the distance.

In this way, the distance between Pt and Pp1 and the distance between Pt and Pp2 are kept constant, and the position is controlled so as to be Dp. That is, the angle control of the curved portion 13 is performed by visual feedback control, and the control of the root position Pp of the curved portion 13 is performed by position control.

The arm control accuracy (difference between the amount actually driven and the detected amount) and the curvature control accuracy (difference between the actual curvature amount and the detected curvature amount) affect the distance measurement accuracy. The extent of the effect depends on the operation amount of the endoscope and the distance to the target.

As described above, according to the present application, it is possible to measure the distance between the endoscope (imaging portion) and the observation target without obstructing the operator's concentration and the operator's field of view. In addition, precise visual field operation in consideration of distance, position information, etc. is realized, and it is possible to perform a look-around operation while keeping the distance to the observation target constant.

The operation modes include a mode in which the endoscope is moved without visual feedback control and distance measurement (normal operation mode), a mode in which visual feedback control (lock-on) is performed, and a mode in which the position is controlled so that the distance between the distal end of the endoscope and the observation target is constant. The mode switching (transition) may be determined by the system according to the scene, or may be operated by the operator with a switch.

The flow of a series of procedures related to lock-on is as follows. When observing the target organ (observation target) on the screen from a predetermined distance and angle, the distance to the observation target is measured by the distance measurement flow shown in FIG. 6. If the target moves during distance measurement, the distance measurement error determination means notifies the user of the error. In case of an error, distance measurement is performed again if necessary. As a result, the position of the observation target can be known from the distance information and the position information of the distal end of the endoscope. Then, based on the position information of the observation target, the moving destination (moving path if necessary) of the distal end of the endoscope is determined, and the arm is controlled to move the distal end of the endoscope to the moving destination.

Figure 11A:
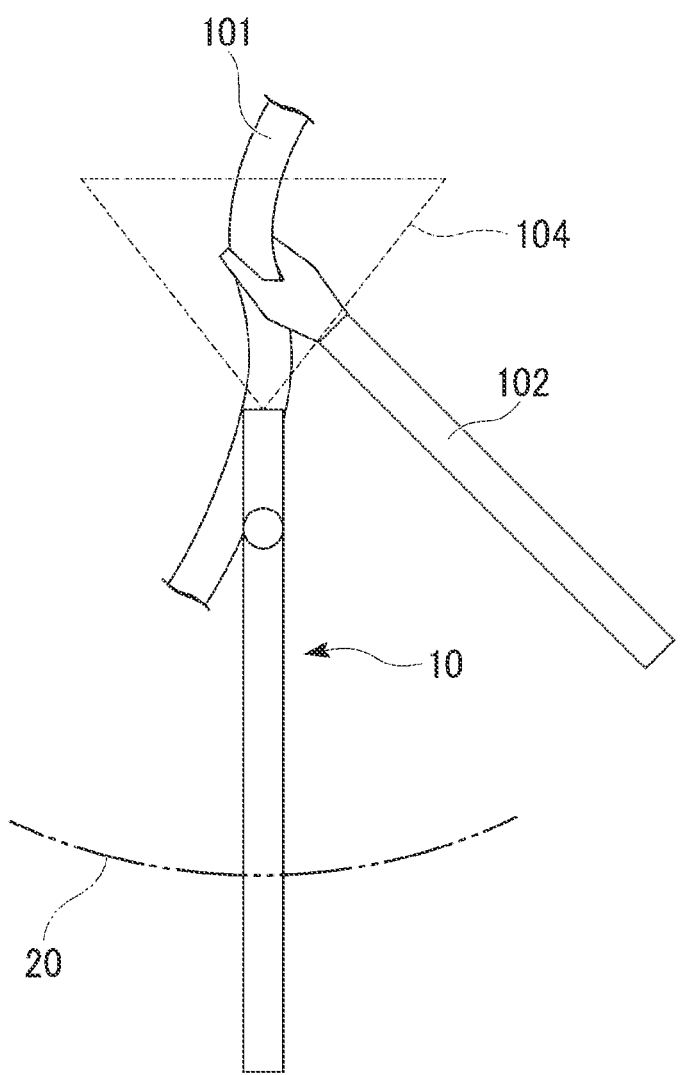
FIG. 11A is a diagram showing a flow of capturing a scene of clipping a blood vessel using the endoscope according to the embodiment of the present invention.

FIGS. 11A to 11D are diagrams showing a flow of imaging a scene of clipping a blood vessel. In the scene where the blood vessel 101 is clipped, as shown in FIG. 11A, when the operator grasps the blood vessel 101 with the clip applier 102, the system recognizes the scene based on the endoscopic image, and it is determined that the visual field 104 should be changed so that whether or not the clip applier 102 properly sandwiches the blood vessel 101 can be confirmed. It should be noted that AI or the like may be used for scene recognition and visual field change determination based on the image.

Figure 11B:
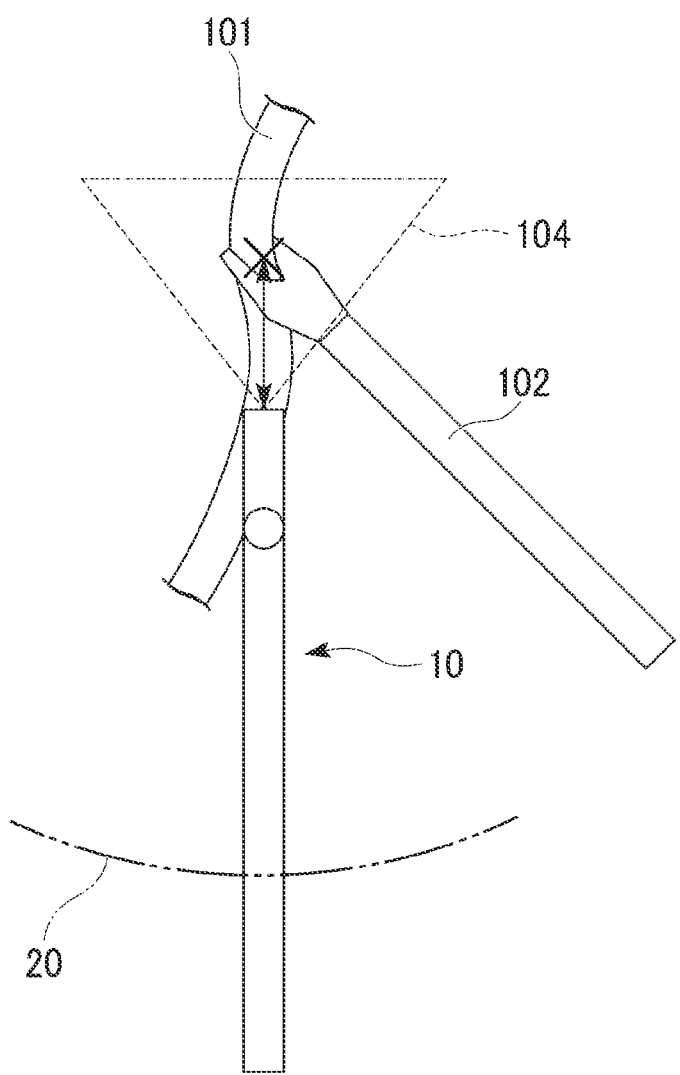
FIG. 11B is a diagram showing a flow of capturing a scene of clipping the blood vessel using the endoscope according to the embodiment of the present invention.
Figure 11C:
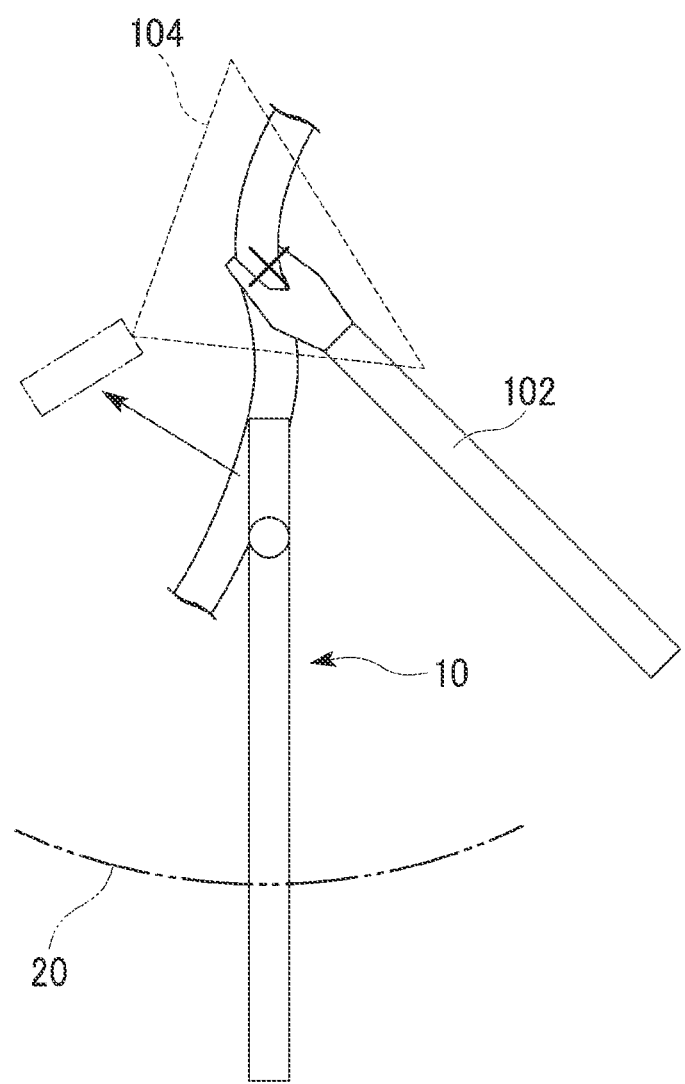
FIG. 11C is a diagram showing a flow of capturing a scene of clipping the blood vessel using the endoscope according to the embodiment of the present invention.

The system drives the arm and the curved portion of the endoscope, and as shown in FIGS. 11B and 11C, while maintaining the observation target 103 (here, the tip of the clip) to be observed at the center of the screen, acquires the distance information between the distal end of the endoscope and the observation target 103 according to the distance measurement flow shown in FIG. 6. Then, the system calculates the position of the observation target 103 based on the distance information, and determines the position of the moving destination of the distal end of the endoscope and the optical axis direction to the observation target 103 based on the position information and the image information.

Figure 11D:
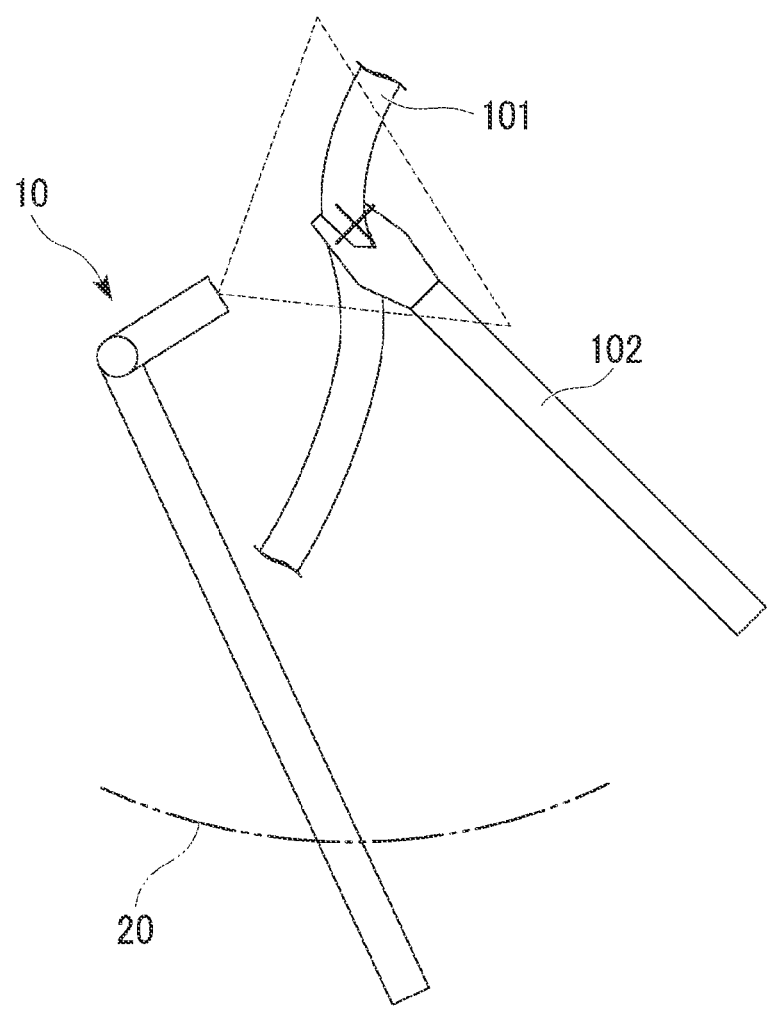
FIG. 11D is a diagram showing a flow of capturing a scene of clipping the blood vessel using the endoscope according to the embodiment of the present invention.
Figure 12:
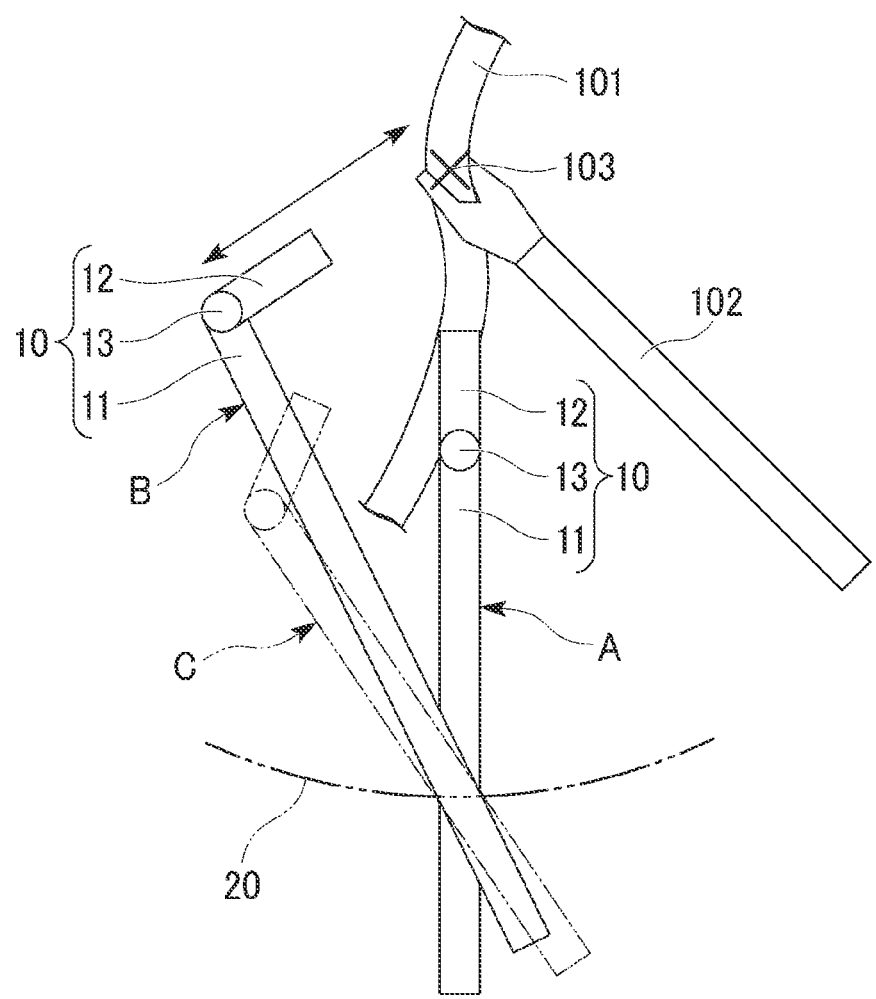
FIG. 12 is a diagram showing an example of a positional relationship between the endoscope and the observation target in a patient's body.

Then, the system notifies the operator to change the visual field 104, and after obtaining the operator's consent, moves the distal end of the endoscope as shown in FIG. 11D. As a result, the operator can perform the procedure with an optimal field of view without disturbing the concentration of the operator.

As described above, in the present invention, the observation target is continuously captured in the center of the screen by the visual feedback control, and based on the operating angle (pivot angle) of the endoscope and the curvature angle of the curved portion (distal end of the endoscope) at that time, the distance to the observation target is measured. Based on the movement of the observation target on the screen and the movement of the endoscope, it is determined whether or not the observation target itself is moving. When it is determined that the observation target is moving, it is determined that the distance measurement result is incorrect, and the distance measurement can be stopped.

Since the distance to the observation target is calculated based on image processing and joint angles inside and outside the body cavity, no special sensor (high-precision, high-cost ranging sensor, etc.) is required at the distal end of the endoscope.

When measuring the distance to the observation target (affected part) imaged by the (monocular) endoscope, a predetermined motion is performed using visual feedback control, and the distance is calculated from the images before and after the predetermined motion. Since the visual feedback control keeps the observation target at an arbitrary position on the screen, it does not interfere with the operator's concentration during distance measurement. In this way, the distance from the distal end of the endoscope to the observation target can be measured in the body cavity without the operator (observer) feeling uncomfortable with the image change during a predetermined operation.

Although one embodiment of the present invention has been described above, the technical scope of the present invention is not limited to the above embodiment, and the combination of components may be changed and various changes may be made to or deleted from each component without departing from the spirit of the present invention.

Each component is for explaining the function and processing related to each component. A single configuration may simultaneously realize functions and processes related to a plurality of components.

Each component such as a controller, a control means, a distance-measuring means, a distance measurement error determination means, and a system may be realized by a computer consisting of, for example, one or a plurality of processors, logic circuits, memories, input/output interfaces, and a computer-readable recording medium as a whole. In that case, the above-described various functions and processes may be realized by recording a program for realizing each component or the entire function on a recording medium, reading the recorded program into a computer system, and executing the program.

In this case, for example, the processor is at least one of a CPU, a DSP (Digital Signal Processor), and a GPU (Graphics-Processing Unit). For example, the logic circuit is at least one of an ASIC (Applicaion-Specific Integrated Circuit) and an FPGA (Field-Programmable Gate Array).

Further, the "computer system" referred to here may include hardware such as an OS and peripheral devices. Further, the "computer system" includes a homepage-providing environment (or a display environment) if a WWW system is used. The "computer-readable recording medium" includes a writable non-volatile memory such as a flexible disk, a magneto-optical disk, a ROM, and a flash memory, a portable medium such as a CD-ROM, and a storage device such as a hard disk built into a computer system.

Further, the "computer-readable recording medium" also includes those that hold the program for a certain period of time, such as a volatile memory (for example, DRAM (Dynamic Random-Access Memory)) inside a computer system that serves as a server or a client when a program is transmitted via a network such as the Internet or a communication line such as a telephone line.

Further, the program may be transmitted from a computer system in which this program is stored in a storing part device or the like to another computer system via a transmission medium or by a transmission wave in the transmission medium. Here, the "transmission medium" for transmitting a program refers to a medium having a function of transmitting information, such as a network (communication network) such as the Internet or a communication line such as a telephone line. Further, the above program may be for realizing some of the above-described functions. Further, it may be a so-called difference file (difference program) that realizes the above-described function in combination with a program already recorded in the computer system.

The present invention can be widely applied to endoscopic systems, and by using visual feedback control to maintain a state in which the target position is captured even when the endoscope is curved, the distance to the target can be calculated without disturbing the operator's concentration, and the procedure can be performed with the optimum field of view.

What is claimed is:

1. A distance-measuring method for use with an endoscope inserted into a body cavity via a trocar, the endoscope including a distal end portion having an imaging portion and an elongated portion having a curved portion, wherein the distance-measuring method includes: acquiring a first curvature angle of the curved portion in a first state in which the endoscope is inserted into the body cavity and captures an observation target; acquiring a second curvature angle of the curved portion in a second state in which an insertion direction of the endoscope is changed with a position of the trocar as a pivot point while capturing the same observation target as in the first state; acquiring a change amount in an insertion angle due to a change in the insertion direction; acquiring a first insertion amount of the endoscope from the pivot point of the trocar to the curved portion in the first state; acquiring a second insertion amount of the endoscope from the pivot point of the trocar to the curved portion in the second state; calculating a distance between the distal end portion and the observation target, wherein the calculating comprises: defining a polygon using the first curvature angle, the second curvature angle, the change amount in the insertion angle, the first insertion amount, the second insertion amount, and a length of the distal end portion; and calculating the distance between the distal end portion and the observation target by applying a formula comprising principles of trigonometry to a triangle that is part of the polygon.

2. The distance-measuring method according to claim 1, wherein the polygon comprises a first triangle having the observation target as one of its apexes and a second triangle having the pivot point as one of its apexes.

3. The distance-measuring method according to claim 2, further comprising:
calculating an angle of the apex of the first triangle where the observation target is located, based on change amounts in the first curvature angle, the second curvature angle, and the insertion angle.

4. The distance-measuring method according to claim 1, wherein in the first state the elongated portion and the curved portion extend in a straight line to the observation target.

5. The distance-measuring method according to claim 1, wherein the principles of trigonometry comprises a calculation using trigonometric functions.

6. The distance-measuring method according to claim 5, wherein the calculation using trigonometric functions comprises the law of cosines and the law of sine.

7. The distance-measuring method according to claim 6, wherein the calculation using trigonometric functions comprises a process applying the law of sine to a triangle having the observation target as one of its apexes and a process applying the law of cosines to a triangle having the trocar as one of its apexes.

8. An endoscope system comprising: an endoscope having a distal end portion having an imaging portion and an elongated portion having a curved portion, the endoscope is inserted into a body cavity via a trocar, and a controller, the controller being configured to: acquire a first curvature angle of the curved portion in a first state in which the endoscope is inserted into the body cavity and captures an observation target, acquire a second curvature angle of the curved portion in a second state in which an insertion direction of the endoscope is changed with a position of the trocar as a pivot point while capturing the same observation target as in the first state, acquire a change amount in an insertion angle due to a change in the insertion direction, and acquire a first insertion amount of the endoscope from the pivot point of the trocar to the curved portion in the first state, acquire a second insertion amount of the endoscope from the pivot point of the trocar to the curved portion in the second state, and calculate a distance between the distal end portion and the observation target, wherein the calculating comprises: define a polygon using the first curvature angle, the second curvature angle, the change amount in the insertion angle, the first insertion amount, the second insertion amount, and a length of the distal end portion; and calculate the distance between the distal end portion and the observation target by applying a formula comprising principles of trigonometry to a triangle that is part of the polygon.

9. The endoscope system according to claim 8, wherein the polygon comprises a first triangle having the observation target as one of its apexes and a second triangle having the pivot point as one of its apexes.

10. The endoscope system according to claim 9, wherein the controller calculates an angle of the apex of the first triangle where the observation target is located based on change amounts in the first curvature angle, the second curvature angle, and the insertion angle.

11. The endoscope system according to claim 8, wherein
wherein in the first state the elongated portion and the curved portion extend in a straight line to the observation target angle.

12. The endoscope system according to claim 8, wherein the controller calculates a result of statistical processing from a plurality of distances calculated by repeating a series of processes a plurality of times as the distance.

13. The endoscope system according to claim 8, wherein the controller calculates the distance when an operation input by an operator is not performed for a predetermined time or more.

14. The endoscope system according to claim 8, wherein the principles of trigonometry comprises a calculation using trigonometric functions.

15. The endoscope system according to claim 14, wherein the calculation using trigonometric functions comprises the law of cosines and the law of sine.

16. The endoscope system according to claim 15, wherein the calculation using trigonometric functions comprises a process applying the law of sine to a triangle having the observation target as one of its apexes and a process applying the law of cosines to a triangle having the trocar as one of its apexes.

* * * * *